United States Patent [19]

March et al.

[11] Patent Number: 5,116,864

[45] Date of Patent: May 26, 1992

[54] METHOD FOR PREVENTING RESTENOSIS FOLLOWING RECONFIGURATION OF BODY VESSELS

[75] Inventors: Keith L. March, Carmel; David R. Hathaway; Robert L. Wilensky, both of Indianapolis; Brian L. Patton, Thorntown, all of Ind.

[73] Assignee: Indiana University Foundation, Bloomington, Ind.

[21] Appl. No.: 682,627

[22] Filed: Apr. 9, 1991

[51] Int. Cl.$^5$ ............................................. A61K 31/35
[52] U.S. Cl. ..................................................... 514/455
[58] Field of Search ......................................... 514/455

[56] References Cited

U.S. PATENT DOCUMENTS

| | | | |
|---|---|---|---|
| 4,169,204 | 9/1979 | Hearst et al. | 546/270 |
| 4,269,851 | 5/1981 | Kaufman | 514/455 |
| 4,269,852 | 5/1981 | Kaufman | 514/455 |
| 4,294,822 | 10/1981 | Kaufman | 424/59 |
| 4,321,919 | 3/1982 | Edelson | 128/214 R |
| 4,328,239 | 5/1982 | Kaufman | 514/455 |
| 4,464,354 | 8/1984 | Bisagni | 424/59 |
| 4,465,691 | 8/1984 | Bisagni et al. | 514/455 |
| 4,512,762 | 4/1985 | Spears | 604/21 |
| 4,577,636 | 3/1986 | Spears | 128/654 |
| 4,753,958 | 6/1988 | Weinstein | 514/410 |
| 4,771,777 | 9/1988 | Horzewski et al. | 128/344 |
| 4,773,899 | 9/1988 | Spears | 604/20 |
| 4,790,315 | 12/1988 | Mueller et al. | 128/344 |
| 4,799,479 | 1/1989 | Spears | 128/303.1 |
| 4,824,436 | 4/1989 | Wolinsky | 604/53 |
| 4,878,492 | 11/1989 | Sinofsky et al. | 128/303.1 |
| 4,892,519 | 1/1990 | Songer et al. | 604/96 |
| 4,983,625 | 1/1991 | Shroot et al. | 514/455 |

OTHER PUBLICATIONS

Dartsch et al., Differential Effect of Photofrin II . . . , Arteriosclerosis 10:616 (1990).
Dartsch et al., Responses of Cultured Smooth Muscle Cells . . . , J. Am. Coll. Cardiol., 15:1545 (1990).
Benson, Treatment of Diffuse Transitional Cell Carcinoma . . . , J. Urol. 134:675, 678 (1985).
Dougherty et al., Photoradiation Therapy for the Treatment . . . , Cancer Res. 38:2628 (1978).
Lam et al., Detection of Early Lung Cancer Using Low Dose . . . , Chest 97:333 (1990).
Prout et al., Photodynamic Therapy with Hematoporphyrin . . . , New Eng. J. Med. 317:1251 (1987).
Razum et al., Skin Photosensitivity: Duration and Intensity . . . , Photochem. and Photobiol., 46:925 (1987).
Honigsmann, Photosensitizing Compounds: Their Chemistry . . . , (1989), p. 143 (Wiley).
Harber et al., Photosensitivity Diseases (1989), 69 (Decker).
Stern et al., Psoriasis, Roenigk, Ed. (1991) 604 (Dekker).
Laskin, Psoralens Potentiate Ultraviolet Light-Induced Inhibition . . . , Proc. Natl. Acad. Sci. 83:8211 (1986).
Gasparro, Psoralen DNA Photobiology (CRC Press, 1988).
Anderson et al., Psoralen Photochemistry of Cutaneous Disorders, Ann. Rev. Pharmicol. Toxicol. 20:235 (1980).
Fujii et al., Light-Scattering Properties of a Rough--Ended Optical Fiber, Optics and Laser Technol. 40 (Feb.) 1984.

*Primary Examiner*—Leonard Schenkman
*Attorney, Agent, or Firm*—Baker & Daniels

[57] ABSTRACT

Restenosis following vascular recanalization is prevented by administering a photoactivatable psoralen and, in conjunction with recanalization, delivering ultraviolet radiation to the region of said recanalization.

20 Claims, No Drawings

METHOD FOR PREVENTING RESTENOSIS FOLLOWING RECONFIGURATION OF BODY VESSELS

BACKGROUND OF THE INVENTION

A number of procedures have been developed to recanalize at least partially occluded blood vessels by dilation or clearing of occlusive material. These procedures utilize, alone or in combination, balloon, laser, thermal, ultrasound, non-balloon mechanical (e.g. atherectomy) or stenting devices. All rely on some form of mechanical violence to the vascular wall which, in early or delayed consequence, produces an undesirably high incidence of restenosis at or near the injured site. This situation prevails despite the high levels of sophistication represented in angioplasty (stenosis reduction) device technology and its application.

Numerous studies have implicated the uncontrolled proliferation of smooth muscle cells within the arterial wall resulting from injury initiated by angioplasty as a prominent factor in restenosis as well as the formation of the initial atherosclerotic lesion. Included in approaches to the problem of the initial occlusion have been attempts to achieve inhibition of smooth muscle cell proliferation by administration of photoactivatable chemical agents which provide some degree of cytotoxic reaction. This work has chiefly centered on hematoporphyrin and its derivatives. For example, dihematoporphyrin ester and ether exhibit greater inhibition of plaque cell proliferation in culture than proliferation of smooth muscle cells derived from nonatherosclerotic arteries, suggesting an increased activity against plaque cells. Dartsch et al., *Differential Effect of Photofrin II On Growth Of Human Smooth Muscle Cells From Nonatherosclerotic Arteries And Atheromatous Plaques In Vitro*, Arteriosclerosis 10:616 (1990). Also, ultraviolet radiation of hematoporphyrin ester and ether has been found to intensify destruction of smooth muscle cells from atherosclerotic plaque as compared with nonatherosclerotic arterial cells. Dartsch et al., *Responses Of Cultured Smooth Muscle Cells From Human Nonatherosclerotic Arteries And Primary Stenosing Lesions After Photoradiation: Implications For Photodynamic Therapy of Vascular Stenoses*, J. Am. Coll. Cardiol. 15:1545 (1990).

Other laboratory studies have demonstrated selective absorption of hematoporphyrins by atheromatous plaques which, on irradiation, induce fluorescence that permits imaging of the plaques. U.S. Pat. No. 4,577,636 (Spears). Animal studies have produced proposals for the destruction of atheromatous plaque by photoactivated hematoporphyrins. U.S. Pat. Nos. 4,512,762 and 4,773,899 (Spears).

Despite promising laboratory results on the selective inhibition or destruction of atheromatous plaque, inherent properties of hematoporphyrins have mitigated against their use in humans. Numerous reports of treatment of various cancers have established the significant cytotoxic effect of hematoporphyrins as well as the need for caution to avoid cutaneous phototoxicity from systemic hematoporphyrin administration. In one study it was found that patients needed protection from light exposure "for several weeks after therapy" with systemic hematoporphyrin derivative in patients with diffuse transitional cell carcinoma of the bladder. Benson, *Treatment of Diffuse Transitional Cell Carcinoma in situ by Whole Bladder Hematoporphyrin Derivative Photodynamic Therapy*, J. Urol. 134:675, 678 (1985). To the same effect with respect to duration of generalized photosensitization of patients in cancer therapy, see Dougherty et al., *Photoradiation Therapy for the Treatment of Malignant Tumors*, Cancer Res. 38:2628 (1978) ("up to 30 days"); Lam et al., *Detection of Early Lung Cancer Using Low Dose Photofrin II*, Chest 97:333 (1990) ("a minimum of 30 days"); Prout et al., *Photodynamic Therapy With Hematoporphyrin Derivative in the Treatment of Superficial Transitional Cell Carcinoma of the Bladder*, New Eng. J. Med. 317:1251 (1987) ("four to six weeks"); and Razum et al., *Skin Photosensitivity: Duration and Intensity Following Intravenous Hematoporphyrin Derivates, HpD and DHE*, Photochem. and Photobiol. 46:925 (1987) ("7 weeks").

Although the hematoporphyrins have thus been shown to inhibit smooth muscle cell proliferation and to possess other qualities that would be useful in defending against atherosclerosis, the phototoxicity of hematoporphyrins does not commend its human use based on present knowledge in the art. Indeed, there is no currently available and practicable method for diminishing or prophylaxing the restenotic process.

It is, therefore, an object of this invention to provide a novel approach to preventing restenosis following recanalization of peripheral and cardiac vasculature by angioplasty, including dilation or clearing of occlusive material.

It is also an object to provide a photochemotherapeutic approach to preventing restenosis following such recanalization of peripheral and cardiac vasculature by conjunctive systemic administration of a photoactivatable agent with little cytotoxic effect which inhibits proliferation of smooth muscle cells on ultraviolet radiation.

It is a further object to provide a method for preventing restenosis following recanalization of peripheral and cardiac vasculature using intraluminal catheters for delivering ultraviolet light to an arterial site at which a systemically administered psoralen is present in smooth muscle cells subject to hyperproliferation in the region of dilation.

It is an additional object to provide a method for preventing restenosis following coronary artery reconfiguration by balloon angioplasty in which a photoactivatable psoralen is delivered to the smooth muscle cells in the presence of ultraviolet radiation as a means for inhibiting smooth muscle cell proliferation in the region of coronary angioplasty.

SUMMARY OF THE INVENTION

It has now been discovered that photoactivatable psoralens significantly inhibit the proliferation of smooth muscle cells on irradiation with long-wave ultraviolet light (PUVA). Accordingly, this invention relates to a method for preventing restenosis in a subject undergoing vascular recanalization which comprises administering a photoactivatable psoralen, reconfiguring at least a partially-occluded vessel, and delivering ultraviolet radiation to the region of recanalization. By recanalization is meant a procedure for increasing blood flow through the occluded vessel by angioplasty, including dilation or ablation or removal of occlusive material.

This novel method may be used with any form of recanalization of peripheral or cardiac vasculature utilizing, alone or in combination, balloon, laser, thermal, ultrasound, non-balloon mechanical (e.g. atherectomy)

or stenting devices. Conditions such as coronary artery occlusion, peripheral artery occlusion, arterial or venous graft occlusion and synthetic graft occlusion are appropriate candidates for treatment by the method of this invention.

DESCRIPTION OF THE INVENTION

The discovery that photoactivatable psoralens significantly inhibit the proliferation of smooth muscle cells on irradiation with ultraviolet light is a signal development in view of the fact that there is no currently available and practicable method for diminishing or prophylaxing the restenotic process in humans. The extensive recorded history of the use of systemically administered psoralens as the treatment of choice in psoriasis provides confidence that psoralens will find a significant place in preventing restenosis where smooth muscle cell proliferation is implicated as a causative factor.

Psoralens are known to provide workable safety margins with ultraviolet radiation in the A band range (PUVA) of about 320 to about 400 nm. The relatively short period of light sensitivity in subjects who have received psoralens and artificial PUVA (as compared, for example, with the prolonged sensitivity associated with the hematoporphyrins) is documented in numerous studies on the treatment of psoriasis and provides evidence that use of their combination as an adjunct to vascular recanalization in the prevention of restenosis presents no untoward complications. Psoralens are said to be cleared from the body in about 24 hours, with no photosensitivity inducible after 8 hours. Honigsmann, *Photosensitizing Compounds: Their Chemistry, Biology and Clinical Use* (1989), p. 143 (Wiley). Manifestations of previously induced photoxicity have been reported as inflammation peaking at 48-72 hours. Harber et al., *Photosensitivity Diseases* (1989), 69 (Decker); Stern et al., *Psoriasis*, Roenigk, Ed. ( 1991) 604 (Dekker).

There has been wide speculation as to the mode of action of psoralens photoactivated by ultraviolet light in the treatment of psoriasis. It is known that photoactivated psoralens may form links with DNA to affect cell growth. Also, effects of UVA light on epidermal growth factor receptor binding is potentiated by psoralens. Laskin, *Psoralens Potentiate Ultraviolet Light-Induced Inhibition of Epidermal Growth Factor Binding*, Proc. Natl. Acad. Sci. 83:8211 (1986). However, the mechanism by which irradiated psoralens inhibit smooth muscle cell proliferation has not been elucidated and is not advanced by the modulation of epithelial cell growth.

The molecular structure of psoralen admits of multisubstitution at numerous positions. Although in the practice of this invention, 8-methoxypsoralen is preferred, unsubstituted psoralen and other-substituted photoactivatable psoralens, identified by their ability to undergo bonding with cellular macromolecules (e.g., DNA) and inhibit smooth muscle cell proliferation are appropriate for use herein. Examples of such psoralens are those substituted at one or more of the 3, 4, 4', 5, 5' or 8 positions, such as 5-methoxypsoralen, 4-methylpsoralen, 4,4'-dimethylpsoralen, 4,5'-dimethylpsoralen, 4',8-dimethylpsoralen and 4,5',8-trimethylpsoralen. These further include pyridopsoralens, 3-carbethoxy psoralens, 4'-lower alkoxy psoralens, 4-lower alkyl-8-amino-lower alkyl psoralens, 5' amino-alkyl psoralens and iso-psoralens (angelicins), as described in Gasparro, *Psoralen DNA Photobiology* (CRC Press, 1988) and U.S. Pat. Nos. 4,321,919 (Edelson), 4,465,691 (Bisagni), 4,269,851 (Kaufman), 4,328,239 (Kaufman), 4,269,852 (Kaufman), 4,464,354 (Bisagni), 4,294,822 (Kaufman) and 4,169,204 (Hearst), disclosure of which are incorporated herein by reference.

It is the psoralen's basic structure which confers the desired activity, with substituents enhancing or diminishing photoactivation and photosensitization. Accordingly, giving consideration to these variables and possible idiosyncratic reactions to specific substituents, a wide range of selection is afforded by this class of compounds. Helpful discussions of the chemistry and photochemotherapy of psoralens and structures of other psoralens for consideration in this use found in Harber et al., *Photosensitivity Diseases* (1989), Chapter 6 (Decker), and Anderson et al., *Psoralen Photochemotherapy of Cutaneous Disorders*, Ann. Rev. Pharmicol. Toxicol. 20:235 (1980).

The objective in psoralen administration is to achieve quickly the serum levels of psoralen found appropriate for light-dependent inhibition of smooth muscle cell growth. Should recanalization be recognized as immediately necessary during catheterization but before peak levels of psoralen are obtained, recanalization should proceed and be followed at the time of peak levels by a separate procedure directed to preventing restenosis.

Administration preferably is systemic by oral dosage to achieve serum levels from about 0.1 to about 10 $\mu$M, preferably from about 0.5 to about 2 $\mu$M, at which time radiation would be commenced. Individual doses in the range of from about 10 to about 100 mg in a single dose given about 30 minutes to 3 hours, preferably 1 to 2 hours, prior to arterial dilation are appropriate. Single doses of from about 20 to about 70 mg given about one-half to about 1 hour prior to the procedure are preferred. Alternatively, a single intravenous injection to give corresponding serum levels may be given about one-half hour before the procedure where oral administration is not feasible. Another alternative is the local intra-arterial injection of a psoralen via catheters such as those employed for delivering heparin, as described in U.S. Pat. No. 4,824,436 (Wolinsky).

Catheters appropriate for use in accomplishing vascular recanalization and affording properly focused ultraviolet radiation are exemplified by those catheters described for use in laser balloon angioplasty, in which provision for radiation to heat the area of dilation is incorporated. Such a catheter is described in U.S. Pat. No. 4,799,479 (Spears), which is incorporated herein by reference. It is advantageous to employ a catheter with fiber-optics for transmission of the radiation that permits 360° exposure of the endoluminal surface of the artery to ultraviolet light. The typical fiber-optic employed in laser angioplasty may be adapted for present use by abrading at least a portion of the fiber-optic surface within the reconfiguring element (e.g., balloon). U.S. Pat. Nos. 4,799,479 (Spears), 4,878,492 (Sinofski); Fujii et al., *Light-Scattering Properties of a Rough-Ended Optical Fiber*, Optics and Laser Technol. 40 (Feb.) 1984. This permits diffusion of radiation along the optical fiber instead of solely out the distal end, thus affording radiation at, rather than along, the targeted vascular surface.

It may be desirable to employ a catheter providing flow-through of arterial blood in order to avoid undue artificial occlusion during the process of recanalization and smooth muscle cell inhibition. In such event, perfusion catheters such as described in U.S. Pat. Nos. 4,771,777 (Horzewski), 4,790,315 (Mueller) and 4,892,519 (Songer), modified to receive the fiber-optic for UVA transmission, may be employed.

Energy delivery at the catheter tip ranges from about 0.1 to about 10 J/cm$^2$, although empirical derivation can identify more precise levels. For example, if deeper effect is desired, elevated energy levels might be necessary to compensate for superficial absorbance of UV energy resulting from attenuation. Another variable is the rate of energy delivery. In order to minimize occlusion time of the vessel during energy delivery, delivery time should be judged by the condition of the patient and other factors.

As a guide, the power input in W/cm$^2$ should be the desired J/cm$^2$ divided by the time in seconds. For example, 5 J/cm$^2$ desired over 5 seconds would require a power output of 1 W/cm$^2$. The power input at the proximal tip of the catheter would be determined by the area of illumination in cm$^2$, the catheter length-attenuation constant, any focal losses at optical joints, and any attenuation determined to occur through the balloon and the substance used for inflation. Generally, irradiation of a circumferential area of vessel wall of about 1.5 cm$^2$, delivered from the working area of the optical fiber, would require from about 0.15 to about 15 J in an appropriate combination of time and power. For example, 10 J over a period of 10 seconds would require 1 W of power. Expressed in terms of the reciprocal relationship between power and time, exposure for 10 to 100 seconds would require power of 1 W to 0.1 W.

The discovery that the proliferation of smooth muscle cells is inhibited by photoactivating the reaction between a psoralen and smooth muscle cells has been demonstrated in studies of the effects of PUVA exposure on proliferation of bovine aortic smooth muscle cells. Observations were made over a 14-day period by trypan blue exclusion counts to determine cell proliferation and viability. Cell cycle effects were evaluated by thymidine incorporation and flow cytometry with DNA quantitation following the addition of serum to subconfluent cells synchronized by serum withdrawal.

No effect was observed following exposure of the cells to only 8-methoxypsoralen at concentrations up to 10 $\mu$M or only UVA irradiation at energies up to 2 J/cm$^2$. Long-wave UV radiation and 8-methoxypsoralen were found to behave synergistically as potent inhibitors of DNA synthesis of the smooth muscle cells with the EC$_{50}$ in combinations ranging from 7 $\mu$M at 0.22 J/cm$^2$ to 0.2 $\mu$M at 1.4 J/cm$^2$. Similar antiproliferative effects were obtained by inverse variation of dose and energy.

Following serum stimulation, inhibition of DNA synthesis was found with either immediate or delayed (16 hours) application of PUVA. This was independent of subsequent 8-methoxypsoralen washout. Flow cytometry showed this effect to occur via a block prior to S-phase in the synchronized cells. Evaluation of [125]-I-labeled platelet-derived growth factor (PDGF) binding revealed no effect of PUVA on the apparent number or affinity of binding sites present. Cell counting after a single exposure to PUVA (1 $\mu$M, 1 J/cm$^2$) revealed complete arrest of cell proliferation over a 14-day period without additional radiation. No increase in trypan-positive cells was noted over this period. These results show local inhibition of proliferation of vascular smooth muscle cells in culture without evidence of increased cell death relative to untreated cells.

It is known that injury to the components of the vascular wall plays a central role in inciting the smooth muscle proliferative response resulting in restenosis. It is therefore important to utilize antiproliferative agents in a manner achieving smooth muscle cell inhibition without undesirable cell destruction.

It will be appreciated by those in the art that the timing of the administration of a photoactivatable psoralen may vary with factors present at the time of the procedure. For example, the psoralen may be given either before or after recanalization. The important determinant is not the sequence of psoralen administration and recanalization but rather the essential presence of psoralen in the target tissue at the time of ultraviolet radiation. Considerations such as the route of administration of the psoralen, with the consequent variation in transport time to the desired site, against the practicalities facing the physician in a particular situation properly control the sequence. Those skilled in the art will recognize additional variations which may be interposed but which do not depart from the spirit or intent of this invention.

We claim:

1. A method for preventing restenosis in peripheral or cardiac vasculature following vascular recanalization which comprises:
   (a) systemically administering a photoactivatable psoralen to a subject undergoing vascular recanalization said psoralen being administered in a safe and effective amount to achieve serum levels of psoralen appropriate for light-dependent inhibition of smooth muscle cell growth,
   (b) recanalizing at least a partially-occluded vessel, and
   (c) delivering ultraviolet radiation to the region of said recanalization in the presence of said psoralen.

2. The method of claim 1 in which the psoralen is substituted at one or more of the 3, 4, 4', 5, 5' or 8 positions.

3. The method of claim 2 in which the substituents are methyl or methoxy.

4. The method of claim 3 in which the psoralen is 8-methoxypsoralen.

5. The method of claim 1 in which the psoralen is administered orally.

6. The method of claim 5 in which the ultraviolet radiation is from about 320 to about 400 nm.

7. The method of claims 1-6 in which the sequence of steps (a) and (b) is reversed.

8. A method for preventing restenosis following coronary angioplasty which comprises:
   (a) systemically administering a photoactivatable psoralen to a subject undergoing coronary angioplasty said psoralen being administered in a safe and effective amount to achieve serum levels of psoralen appropriate for light-dependent inhibition of smooth muscle cell growth,
   (b) reconfiguring at least a partially-occluded coronary artery by coronary angioplasty, and
   (c) delivering ultraviolet radiation by fiber-optic means to the endoluminal surface of the artery in the region of said angioplasty.

9. The method of claim 8 in which the psoralen is substituted at one or more of the 3, 4, 4', 5, 5' or 8 positions.

10. The method of claim 9 in which the substituents are methyl or methoxy.

11. The method of claim 10 in which the psoralen is 8-methoxypsoralen.

12. The method of claim 8 in which the psoralen is administered orally.

13. The method of claim 12 in which the ultraviolet radiation is from about 320 to about 400 nm.

14. The method of claims 8-13 in which the sequence of steps (a) and (b) is reversed.

15. A method for preventing restenosis in peripheral or cardiac vasculature following vascular recanalization which comprises:
(a) systemically administering a photoactivatable psoralen to a subject undergoing vascular recanalization, said psoralen being administered in an amount sufficient to achieve serum levels from about 0.1 to about 10 μM,
(b) recanalizing at least a partially-occluded vessel, and
(c) delivering ultraviolet radiation to the region of said recanalization in the presence of said psoralen.

16. The method of claim 15 in which the psoralen is substituted at one or more of the 3, 4, 4', 5, 5' or 8 positions.

17. The method of claim 16 in which the psoralen is selected from the group of 8-methoxypsoralen, 5-methoxypsoralen, 4-methylpsoralen, 4,4'-dimethylpsoralen, 4,5'-dimethylpsoralen, 4',8-dimethylpsoralen and 4,5',8-trimethylpsoralen.

18. The method of claim 15 in which the psoralen is 8-methoxypsoralen administered systematically in an amount sufficient to achieve serum levels of from about 0.1 to about 10 μM.

19. The method of claims 15-18 in which the ultraviolet radiation is from about 320 to about 400 nm.

20. The method of claims 15-18 in which the sequence of steps (a) and (b) is reversed.

* * * * *